United States Patent
Trager et al.

(10) Patent No.: US 6,669,958 B1
(45) Date of Patent: Dec. 30, 2003

(54) GEL DELIVERY VEHICLES FOR ANTICELLULAR PROLIFERATIVE AGENTS

(75) Inventors: George Trager, San Mateo, CA (US); Richard E. Jones, Palo Alto, CA (US)

(73) Assignee: BioMedicines, Inc., Emervyville, CA (US)

( * ) Notice: Subject to any disclaimer, the term of this patent is extended or adjusted under 35 U.S.C. 154(b) by 0 days.

(21) Appl. No.: 09/505,303

(22) Filed: Feb. 16, 2000

Related U.S. Application Data

(63) Continuation-in-part of application No. 08/803,128, filed on Feb. 20, 1997.

(51) Int. Cl.$^7$ .......................... A61K 9/10; A61K 47/32; A61K 47/44; A61P 35/00
(52) U.S. Cl. ...................... 424/484; 424/487
(58) Field of Search ................. 424/487, 405, 424/409, 423, 448; 514/944; 422/423

(56) References Cited

U.S. PATENT DOCUMENTS

| | | | |
|---|---|---|---|
| 3,888,995 A | | 6/1975 | Katz et al. |
| 4,695,465 A | * | 9/1987 | Kigasawa |
| 4,938,763 A | | 7/1990 | Dunn et al. |
| RE33,375 E | | 10/1990 | Luck et al. |
| 5,051,257 A | | 9/1991 | Pietronigro |
| 5,120,546 A | | 6/1992 | Hansen et al. |
| 5,487,897 A | | 1/1996 | Polson et al. |
| 5,573,781 A | | 11/1996 | Brown et al. |
| 5,744,153 A | | 4/1998 | Yewey et al. |

FOREIGN PATENT DOCUMENTS

| | | |
|---|---|---|
| CA | 1295242 | 2/1992 |
| DE | 3603444 A1 | 8/1987 |
| EP | 0 209 078 | 1/1987 |
| EP | 0 260 645 | 3/1988 |
| WO | 93/16733 | 9/1993 |
| WO | 94/26300 | 11/1994 |
| WO | 96/40086 | 12/1996 |
| WO | 98/26771 | 6/1998 |
| WO | 98/32422 | 7/1998 |

OTHER PUBLICATIONS

Ansel, et al, *Pharmaceutical Dosage Forms and Drug Delivery Systems*, Williams & Wilkins, Baltimore, 6th Edition, 3:76–85; 8:286–336.
Hoover, et al., *Dispensing of Medication*, Mack Publishing, Easton, PA, 8th Edition, 2:60–83; 10:255–295.
Theon et al., "Intratuloral Chemotherapy with Cisplatin in Oily Emulsion in Horses," *JAVMA*, 202(2):261–267 (1993).
Ansel, "Injections, Biological Products, and Sterile Fluids," *Introduction to Pharmaceutical Dosage Forms*, 2nd ed., Lea & Febiger:Philadelphia, pp. 246–286 (1976).
Chemical Abstract No. 237024, vol. 109, No. 26 (Dec. 26, 1988).
Chemical Abstract No. 232317, vol. 105, No. 26 (Dec. 29, 1986).
Andrews et al., "Regional Chemotherapy in an Experimental Model of Wilms' Tumor in Rats," *Cancer Chemother. Pharmacol.*, 23:31–36 (1989).
Turco and King, *Sterile Dosage Forms: Their Preparation and Clinical Application*, 3rd ed. Lea & Febiger:Philadelphia, pp. 17–24 (1987).

* cited by examiner

*Primary Examiner*—Edward J. Webman
(74) *Attorney, Agent, or Firm*—Dorsey & Whitney LLP

(57) ABSTRACT

Methods and compositions are provided for the treatment of a host suffering from a cellular proliferative diease. In the subject methods, antiproliferative agents are administered in a substantially non-aqueous gel delivery vehicle comprising at least one polar organic solvent in combination with one or more thickening agents. The subject methods and compositions provide for the enhanced efficacy of regionally or locally administered antiproliferative proliferative agents.

15 Claims, No Drawings

GEL DELIVERY VEHICLES FOR ANTICELLULAR PROLIFERATIVE AGENTS

This is a continuation-in-part and claims priority to pending application Ser. No. 08/803,128 filed Feb. 20, 1997.

TECHNICAL FIELD

The field of this invention is chemotherapeutic pharmaceutical formulations.

BACKGROUND OF THE INVENTION

In the treatment of cellular proliferative diseases characterized by the abnormal proliferation of cells, such as cancer, psoriasis and hyperplasia, a variety of diverse methods have been developed. These methods include surgery, radiation therapy and immunotherapy. Of increasing interest in the treatment of cancer and other cellular proliferative diseases is the use of chemotherapeutic agents, either alone or in combination with other known treatment methods. In chemotherapy, the chemotherapeutic agents may be administered either systemically or regionally. While systemic administration of a chemotherapeutic agent has proved effective in the treatment of some cancers, there are consequences with this mode of chemotherapeutic agent delivery. For example, in systemic administration, normal tissue quite distal to the target tissue is exposed to the chemotherapeutic agent along with the diseased tissue. Depending on the toxicity of the particular chemotherapeutic agent employed, the consequences of systemic delivery may outweigh the therapeutic benefit of the agent.

Furthermore, some chemotherapeutic agents are poorly water soluble. Thus, to be administered intravenously (one particular mode of systemic administration) steps must be taken to compensate for this poor water solubility, e.g. dilution in large volumes of an aqueous vehicle, use of surfactants, and the like. However, dilution of the drug in this manner can limit the dosage level of the drug that can be achieved in the host blood stream or in proliferative disease tissue. Other factors which can adversely affect the dosage level of drug which is achieved in the blood stream include metabolism, chemical instability and in situ precipitation of the drug. Other problems include adverse effects of the surfactants, etc.

In view of these considerations, there is increasing interest in methods of regional and local administration of chemotherapeutic agents. With these routes of administration, when choosing a suitable formulation consideration must be given to several factors. One factor to be considered is how readily the agent will diffuse from the vehicle into the region of administration or into other regions of the host, thereby causing toxic side effects. Other factors to be considered include the stability and bioavailability of the agent in the particular delivery vehicle formulation.

Thus, there is a continued interest in the identification of new delivery vehicle formulations suitable for the regional and local administration of anticellular proliferative agents to hosts suffering from cellular proliferative diseases. Such delivery vehicles should ideally provide for at least one of enhanced agent efficacy, reduced systemic toxicity, agent stability, and bioavailability at the site of administration.

Relevant Literature

U.S. Patents describing the intratumoral delivery of antineoplastic agents include U.S. Pat. Nos. 5,051,257 and RE 33,375. RE 33,375 describes the use of an aqueous proteinaceous matrix, e.g. collagen matrix, as a chemotherapeutic delivery vehicle. U.S. Pat. No. 4,938,763 reports the preparation of biodegradable implants prepared from thermoplastic systems of non-reactive polymers dissolved in biocompatible solvents.

Intratumoral injections of cisplatin in a sesame oil-water emulsion delivery vehicle is described in Théon et al., J.A.V.M.A. (1993) 202: 261–267. Regional chemotherapy of Wilms' tumors in rats is described in Cancer Chemother. Pharmacol. (1989) 23:31–36.

Non-aqueous, intraperitoneal drug delivery vehicles are described in Ansel, Introduction to Pharmaceutical Dosage Forms (Lea & Freiberger, Philadelphia) (1976) p. 246; Hoover, Dispensing of Medication (Mack Publishing Co.) (1976); and Targo & King, Sterile Dosage Forms, Their Preparation and Clinical Application (Lea & Freiberger, Philadelphia) (1987) pp. 17–24.

A review of pharmaceutical dosage formulations and methods of their preparation is provided in Ansel et al., Pharmaceutical Dosage Forms and Drug Delivery Systems (1995).

SUMMARY OF THE INVENTION

Methods and compositions are provided for the treatment of a host with a cellular proliferative disease, wherein at least one antiproliferative agent is administered to the host in a substantially non-aqueous, gel delivery vehicle capable of enhancing the efficiency of the agent. The vehicles employed in the subject invention are pharmaceutically acceptable and comprise at least one polar organic solvent in combination with at least one thickening agent. The subject methods and compositions find use in the treatment of a variety of cellular proliferative diseases, where the subject methods result in at least enhanced efficacy of the administered agent.

DESCRIPTION OF THE SPECIFIC EMBODIMENTS

Methods and compositions are provided for the treatment of a host suffering from a cellular proliferative disease. In the subject methods, substantially non-aqueous gel delivery vehicles are employed for the regional or local administration of one or more antiproliferative agents. The substantially non-aqueous gel delivery vehicles are pharmaceutically acceptable and comprise at least one polar organic solvent in combination with at least one thickening agent. The subject methods and compositions find use in the treatment of a variety of cellular proliferative diseases, and provide for at least enhanced efficacy of the delivered agent.

Critical to the subject methods is the use of a substantially non-aqueous gel vehicle for delivery of the antiproliferative agent. The vehicle formulations are pharmaceutically acceptable when used in accordance with the subject methods. By "substantially non-aqueous" is meant that these vehicles contain no more than about 30% water. More preferably, they will comprise less than about 15% (v/v) water, usually less than about 10% (v/v) water, more usually between 5% and 10% (v/v) water.

The substantially non-aqueous delivery vehicles employed in the subject methods are capable of acting as a depot for one or more cellular antiproliferative agents. As the subject delivery vehicles act as a depot for the agent(s), the dispersion of the agent(s) from the vehicle and site of administration will be retarded or slowed as compared to the dispersion of the agent when delivered in a saline solution.

The delivery vehicles have gel-like consistencies but are sufficiently flowable so as to be capable of local or regional administration through a catheter, needle, or other comparable means of local or regional administration. Generally, the subject vehicles will have a viscosity ranging f 50,000 mPa·sec, usually from about 1,000 to 40,000 mPa·sec, and more usually from about 2,000 to 30,000 mPa·sec, all at a shear rate of 10 sec$^{-1}$.

The gel vehicles of the subject invention will comprise at least one polar organic solvent, where two or more different polar organic solvents may be present in the formulation, usually not more than four polar organic solvents, more usually not more than three polar organic solvents. The organic solvent component will make up the majority of the vehicle formulation and provide for a continuous fluid phase, with the organic solvent component ranging from about 65 to 98% (v/v) of the formulation, usually from about 80 to 98% (v/v) of the formulation, more usually from about 90 to 99.5% (v/v) of the vehicle formulation, most preferably from about 75 or 80% to 99.5% (v/v).

Polar organic solvents that find use in the subject invention are not excessively toxic at the dosage levels at which, as well as the manner in which, they are administered, where "not excessively toxic" intends that the solvents in the subject vehicles do not result in unacceptable systemic toxicity when administered in accordance with the subject invention. Polar organic solvents of interest will be at least somewhat water soluble, having a Hildebrand Solubility Parameter of at least about 7.5 or 8 (cal/cc)$^{1/2}$, usually at least about 9, more usually at least about 10. The solvents will have dipole moments of at least about 1.5 D, usually at least about 2.0 D.

The polar organic solvents may comprise C, N, O, S, H and P, and may be cyclic, usually heterocyclic, and will generally be of low molecular weight, having a molecular weight of greater than about 30 Da, usually greater than about 40 Da, but less than about 500 Da, usually less than about 275 Da and more usually less than about 250 Da. The solvents will generally have from 1 to 12 carbon atoms, usually from 2 to 10 carbon atoms, and more usually from 2 to 8 carbon atoms, and will comprise one or more heteroatoms, typically no more than 8 heteroatoms, usually no more than 6 heteroatoms, and more usually fewer than 4 heteroatoms.

Organic solvents of interest will comprise 1 or more oxygen containing substituent groups, usually no more than 4 oxygen containing substituents, more usually no more than 3 oxygen containing substituents, where oxygen containing substituents include oxy, oxo and acid groups, both organic (e.g. carboxy) and inorganic, e.g. sulphur or phosphorus, and the like, where particular substituent groups of interest include: amides and ureas; esters, e.g. carboxylic esters, carbonate esters; ethers; hydroxy groups, and the like. Preferred oxo substituents include amides, esters, acetals and sulfoxides.

Solvents comprising hydroxy substituents include lower alkanols of from 2 to 4 carbon atoms and 1 to 3 hydroxy groups, usually having no more than 1 hydroxy group for every 1.5 carbon atoms. Lower alkanols of interest include ethanol, 1-propanol, 2-propanol, 1-propen-3-ol (allyl alcohol), propylene glycol, glycerol, 2-methyl-2-propanol, and the like, with ethanol being preferred.

Amides of interest may be cyclic and include both N-substituted and unsubstituted amides, where any N-substituents will usually be alkyls of from 1 to 4 carbon atoms, more usually 1 to 3 carbon atoms. Particular amides of interest include: formamide, methyl formamide, dimethyl formamide, ethyl formamide, diethyl formamide, acetamide, methyl acetamide, dimethyl acetamide, ethyl acetamide, and diethyl acetamide. Cyclic amides (lactams) of interest include 2-pyrrolidone, N-methyl-2-pyrrolidone, and N-ethyl-2-pyrrolidone. Ureas of interest include tetramethyl urea, 1,3-dimethyl-2-imidazolidinone, and the like.

Esters of interest include esters of carboxylic acids as well as esters of inorganic acids. Examples of the former include triacetin, triethyl citrate, ethyl lactate, and the like. Examples of the latter include carbonate esters, where particular carbonate esters include: propylene carbonate, 1,2-butylene carbonate, 2,3-butylene carbonate and the like, with propylene carbonate being preferred. Other solvents of interest finding use in the subject vehicles include dimethyl sulfoxide, diethyl sulfoxide, hexamethyl phosphoramide, pyruvic aldehyde dimethylacetal, dimethylisosorbide and the like.

In the subject vehicle formulations, in combination with the polar organic solvent component will be at least one thickening or gelling agent, where a plurality of thickening agents may be employed, usually not more than 3 different thickening agents, more usually not more than 2 different thickening agents. Thickening agents finding use in the subject vehicles will be those agents capable of substantially increasing the viscosity of the formulation to provide for a vehicle having a viscosity ranging from about 500 to 50,000 mPa·sec, usually from about 1,000 to 40,000 mPa·sec, and more usually from about 2,000 to 30,000 mPa·sec all at a shear rate of 10 sec$^{-1}$. Generally, the thickening agent component of the formulation will range from about 0.5 to 20% (v/v) of the formulation, usually from about 1 to 15% (v/v) of the formulation, more usually from about 2 to 10% (v/v) of the formulation, and most preferably from about 0.5 to 10% of the formulation.

Thickening agents of interest, also known as viscosity enhancing agents, are pharmaceutically acceptable for parenteral use when employed in the subject formulations. Finding use as thickening agents in the subject vehicles are fatty acids and other fatty acid esters, as well as the aluminum and magnesium salts thereof, and biocompatible polymers. Fatty acids that find use as thickening agents in the subject vehicles will generally be naturally occurring fatty acids having 12 to 20 carbon atoms, usually 14 to 18 carbon atoms, where the fatty acids may be saturated or have one or more sites of ethylenic unsaturation, usually not more than 4 sites of unsaturation, more usually not more than 2 sites of unsaturation, where monounsaturated fatty acids are preferred. Specific fatty acids of interest include lauric acid, myristic acid, palmitic acid, stearic acid, palmitoleic acid, linoleic acid, linolenic acid, and the like, particularly oleic acid. Also of interest as thickening agents are the aluminum and magnesium salts of the above fatty acids, usually aluminum salts of the above fatty acids, particularly aluminum monostearate.

Thickening agents of interest also include biocompatible synthetic, naturally occurring or modified naturally occurring polymers capable of imparting the desired viscosity to the delivery vehicles. Polymers finding use as thickening agents in the subject vehicles may be non-crosslinked or where the polymers may be linear or branched, but will usually be linear. Polymers of interest may be homo- or copolymers, where the copolymers may be random or block copolymers, and include proteins such as collagen or gelatin, polysaccharides, polyoxyalkylenes, polyvinyls, and the like.

Polysaccharides finding use may be either naturally occurring or chemically modified versions thereof, particularly modified celluloses, where the modified celluloses will have molecular weights ranging from about 5,000 to 200,000 Da, usually from about 10,000 to 150,000 Da, where the cellulosic backbone may be modified with a variety of different pendant groups, including alkyl groups of from 1 to 4 carbon atoms, usually 1 to 2 carbon atoms, hydroxyalkyl groups of from 2 to 4 carbon atoms, carboxyalkyl groups of from 2 to 4 carbon atoms, and the like. Specific modified celluloses of interest include methyl cellulose, ethyl cellulose, hydroxyethyl cellulose, hydroxypropyl cellulose, hydroxypropyl methylcellulose, carboxymethyl cellulose and the like.

Polyoxyalkylenes of interest include high molecular weight polyoxyethylene compounds, where the compounds may be homopolymers, e.g. polyethylene glycols, or copolymers of oxyethylene and oxypropylene monomeric units, e.g. poloxamers. High molecular weight polyoxyalkylene compounds finding use as thickening agents in the subject invention will generally have a molecular weight of at least about 5,000 Da, usually at least about 7,000 Da, and may be as high as 50,000 Da or higher, but will usually be less than 20,000 Da. For polyoxyalkylene copolymers, the copolymers will generally be block copolymers of polyoxyethylene and polyoxypropylene units, where the polyoxyethylene units will generally range from about 20 to 90% by weight of the polymer.

Other polymers of interest include polyvinyl polymers, such as carboxypolymethylene (carbomer), polyvinylpyrrolidone, polyvinyl acetate, polyvinyl alcohol and the like. Polyvinyl polymers of particular interest include carboxypolymethylene (carbomer), polyvinylpyrolidones (povidones) having molecular weights ranging from about 50,000 to about 500,000 Da.

Of particular interest as substantially non-aqueous delivery vehicles are the following solvent and thickening agent combinations: (1) ethanol thickened with hydroxypropyl cellulose in combination with oleic acid; (2) dimethylacetamide thickened with methyl cellulose, hydroxypropylmethyl cellulose, or carboxypolymethylene; (3) propylene carbonate thickened with polyvinylpyrrolidone; or (4) dimethyl sulfoxide (DMSO) thickened with carboxypolymethylene.

In addition to the polar organic solvent and thickening agent components, the delivery vehicle formulations may further comprise various modifying agents that increase the stability and/or usefulness of the final formulation, where such agents include antibacterial and antimicrobial preservatives, buffers, antioxidants, and other pharmaceutical adjuvants. Antibacterial and microbial agents finding use include benzoic acid, butyl paraben, ethylparaben, methylparaben, propylparaben, sodium benzoate, sodium propionate, benzalkonium chloride, benzethonium chloride, benzyl alcohol, cetylpyridinium chloride, chlorobutanol, phenol, phenylmercuric nitrate, thimerosol, and the like. Antioxidants finding use include ascorbic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate, sodium metabisulfite and the like. Buffering agents of interest include potassium metaphosphate, potassium phosphate, monobasic sodium acetate, sodium citrate anhydrous, sodium citrate dihydrate, and the like. These additional agents, when present, will be no more than about 5% (v/v) of the vehicle formulation, usually no more than about 3% (v/v) of the vehicle formulation, more usually no more 2% (v/v) of the formulation.

Also present in the subject vehicle formulations may be various effector agents which further enhance the efficacy of the anticellular proliferative agents delivered in the vehicle formulation. Effector agents of particular interest include vasomodulators, immune modulators, etc. which are used to affect host responsiveness. Of particular interest are effectors which restrict regional vasculature, e.g. vasoactive agents, either as to growth and/or passage opening, e.g. vasoconstrictive or sympathomimetic agents. These effectors include catecholamines, e.g. epinephrine and its borate ester, norepinephrine, dipivefrin, ephedrine, ergot alkaloids, prostaglandins, angiotensin, and the like. When present in the subject formulation, these effector agents will be at least about 0.005% (w/v) of the formulation, usually at least about 0.01% (v/v) of the formulation and less than about 0.1% (w/v) of the formulation, usually less than about 0.05% (v/v) of the formulation.

The subject vehicle formulations find use in the delivery of a wide variety of antiproliferative agents, where antiproliferative or cytostatic agents of interest are agents that tend to retard cellular activity and multiplication, and are preferably cytotoxic. The subject vehicle formulations may be used to deliver one or a combination of agents, where when a combination of agents are delivered in the subject vehicles, the combination will usually consist of no more than 3 agents, more usually no more than 2 agents. In the antiproliferative composition comprising both the antiproliferative agent and vehicle, the agent will be homogeneously distributed throughout the vehicle formulation, where the agent may be present in solution or as a dispersion, e.g. a coarse dispersion, such as a suspension or emulsion, or a fine dispersion such as a colloidal dispersion, including magmas and gels. The antiproliferative agent will be present in the subject vehicle formulation in amounts ranging from about 0.01 to 100 mg/mL of vehicle formulation, usually from about 0.02 to 50 mg/mL, more usually from about 0.1 to 50 mg/mL of the formulation, depending on the particular agent and delivery vehicle.

Antiproliferative agents of interest include antimetabolites, covalent and non-covalent DNA binding agents, chromatin function inhibiting agents, endocrine function inhibiting agents, naturally occurring antiproliferative agents and derivatives thereof, and the like. Antimetabolites of interest include: folate antagonists, e.g. methotrexate (MTX, amethopterin), trimetrexate (TMQ); pyrimidine antagonists, e.g. fluorouracil (5-FU), fluorodeoxyuridine (FUDR), CB3717, azacytidine (aza-C, 5-AC); purine antagonists, e.g. mercaptopurine (MP, 6-MP), thioguanine (TG, 6-TG), tiazofurin, chlorodeoxyadenosine (CdA), pentostatin (2'-deoxycoformycin, dCF); sugar modified analogs, e.g. cytarabine (ara-C), fludarabine (F-ara-A); ribonucleotide reductase inhibitors, e.g. hydroxyurea (HU); and the like. Covalent DNA-binding agents include: nitrogen mustards, e.g. mechlorethamine (HN2, nitrogen mustard), chlorambucil, melphalan (L-phenylalanine mustard, L-PAM), cyclophosphamide, ifosfamide; aziridines, e.g. thiotepa, altretamine (hexamethylmelamine), mitomycin (mitomycin C); alkane sulfonates, e.g. busulfan, nitrosoureas, e.g. carmustine (BCNU), lomustine (CCNU), semustine (methyl-CCNU), streptozotocin; platinum compounds, e.g. cisplatin (cis-DDP), carboplatin; methylating agents, e.g. dacarbazine, procarbazine; and the like. Hypoxia selective cytotoxics include porfiromycin, nitracrine, nitracrine-oxide, and diynene such as neocarzinostatin and dynemicin; and the like. Non-covalent DNA-binding or DNA intercalating agents include: anthracyclines, e.g. daunorubicin, doxorubicin, idarubicin; mitoxantrone; dactinomycin; bleomycin; plicamycin; and the like. Chromatin function inhibitors include: topoisomerase inhibitors, e.g. epipodophyllotoxins such as etoposide (VP-16) and teniposide (VM-26), amsacrine (m-AMSA), camptothecin (CPT), topotecan (TPT), irinotecan (CPT-11) and other campothecin derivatives; microtubule inhibitors, e.g. vinca alkaloids such as vinblastine, vincristine and vindesine, paclitaxel (taxol); and the like. Endocrine function affecting agents include: glucocorticoids, e.g. prednisone, prednisolone; estrogens, e.g. diethylstilbestrol (DES), ethinyl estradiol; antiestrogens, e.g. tamoxifen; progestins, e.g. medroxyprogesterone, megestrol; androgens, e.g. fluoxymestrone, testosteron; antiandrogens, e.g. cyproterone acetate, flutamide; LHRH (GnRH) agonists, e.g. goserelin, leuprolide; aromatase inhibitors, e.g. aminoglutethimide; adrenocortical suppressors, e.g. mitotane (o,p'-DDD); and the like. Naturally occurring antiproliferative agents include: interferons, (e.g. $\gamma$, $\gamma$-la, $\beta$, $\alpha$, etc.), interleukins (e.g. 2, 4, and 10), TNF-$\alpha$ and -$\beta$, and the like.

The subject antiproliferative compositions may be prepared using conventional methods, where the resultant preparations will generally be sterile and nonpyrogenic.

The antiproliferative compositions having been described, their use in the treatment of a host with a cellular proliferative disease will now be discussed in greater detail. The subject compositions find particular use in the treatment of hosts with cellular proliferative diseases characterized by lesions or solid tumors, such as neoplastic diseases. In the subject methods, the antiproliferative compositions are regionally or locally administered. Thus, the antiproliferative compositions are administered at least proximally to a target site of the host, where "target site" is defined as a location of a lesion associated with the cellular proliferative disease afflicting the host, e.g. a tumor. By "at least proximally" is meant that the composition is administered in apposition to the lesion, such that the dispersion of antiproliferative agent from the composition is localized to the region of the lesion, whereby the concentration of antiproliferative agent in the region of the lesion, as well as in the lesion itself, is significantly greater than the systemic concentration of the agent. Where the composition is administered locally, it will be administered directly at the site of a lesion of cellular proliferative disease, usually intralesionally or intratumorally. Convenient methods of regional or local administration include administration via syringe needle, catheter, trochar, and the like.

Therapies which employ the subject compositions and methods may vary depending on the particular host, the nature of the cellular proliferative disease, the size of the lesion and the like. Thus, the antiproliferative composition may be administered once in a particular therapy, where therapy intends the entire course of treatment of the host, or several times, where the interval between administrations may be a matter of hours, days, or even months.

In the subject methods, the volume of distribution, concentration distribution and total dosage of agent(s) in the composition administered to the host are controlled by varying the compositions and/or the method of administration. This is especially important when using drugs with high toxicity, limited stability in vivo, high cost, etc. As indicated above, the drug concentration, vehicle formulation selection and additives may be varied in relation to the particular indication, host condition, growth stage of the tumor, etc. In addition, the previously mentioned parameters are influenced by providing a single injection or multiple injections into separate regions of the tumor, by controlling the localized temperature and blood circulation at the site of administration to reduce systemic dispersion of the agent, and the like. Generally, the volume and concentration of the subject compositions administered at least proximal to the lesion mass should be sufficient to contact as many abnormal cells as possible with a lethal dosage of agent while minimizing exposure to and/or necrosis of surrounding and/or sensitive normal tissue. The volume of composition administered to the tumor in a particular administration may range from 1 to 100 $\mu$L, usually 10 to 50 $\mu$L per 100 mm$^3$ of treated tissue. The dose of cytostatic agent delivered to a tumor site in a particular administration may range from about 0.01 to 200 mg/kg of host, and will usually range from about 0.1 to 100 mg/kg of host, substantially varying with the particular agent, the nature of the composition and tumor, the host and the like.

Although the effector agents described above may be included within the subject compositions for simultaneous administration, the effectors may also be administered shortly before or after the subject compositions. When the effector agent is administered after administration of the composition, the effector agent will be administered within about 8 hours, preferably within about 4 hours, more preferably within about 2 hours, and most preferably within about 1 hour. Where the effector agent is administered before the subject composition, e.g. in instances where it may be advantageous to "prime" the host with an effector agent, e.g. epinephrine, administration will usually be within about 60 minutes, preferably within about 10 minutes, more preferably within about 2 minutes prior to the administration of the subject compositions.

The subject methods may be used to treat a wide variety of hosts, including mammalian hosts, such as domestic animals, e.g. pets and livestock, rare or exotic animals, and humans. Cellular proliferative diseases amenable to treatment with the subject formulations are diseases characterized by the abnormal proliferation of cells. Diseases characterized by the abnormal proliferation of cells include neoplasia, psoriasis, hyperplasia and the like.

Neoplastic diseases amenable to treatment according to the subject methods include neoplastic diseases characterized by the development of solid tumors or lesions, including solid malignant tumors of the lung, breast, colon, rectum, ovaries, stomach, pancreas, uterus, testicles, brain, liver, head and neck, prostate and the like. Typically, therapeutic gain can be realized with tumors greater than about 50 mm$^3$, particularly with tumors greater than 100 mm$^3$, and more particularly with tumors greater than 200 mm$^3$. Particular neoplastic cellular proliferative diseases that may be treated with the subject methods include carcinomas, sarcomas and melanomas, such as basal cell carcinoma, squamous cell carcinoma, melanoma, soft tissue sarcoma, solar keratoses, Kaposi's sarcoma, cutaneous malignant lymphoma, Bowen's disease, Wilm's tumor, hepatomas, colorectal cancer, brain tumors, mycosis fungoides, Hodgkins lymphoma, polycythemia vera, lymphomas, oat cell sarcoma, superficial and invasive bladder tumors, ovarian cancer, etc.

The effectiveness of the disclosed methods may generally be characterized as reducing the severity of toxicity to tissue surrounding the lesion and reducing tumor burden, reducing host systemic toxicity to the presence of the antiproliferative agent, as well as delaying growth and tumor progression. The disclosed methods generally result in an inhibition in the growth of the proliferative lesion as compared with no treatment, systemic treatment or intralesional treatment with the delivered drug in an aqueous or predominantly aqueous vehicle (i.e., water in an amount in excess of 50%).

Also provided are kits comprising the gel vehicle composition separate from the antiproliferative agent(s), where such kits find use when it is preferable to prepare the formulation immediately prior to use. In addition to the vehicle and antiproliferative agent(s), the kits may further comprise mixing means for preparing the final antiproliferative composition to be administered. For example, the vehicle may be provided in a first container and the active agent(s) in a second container, where the kit comprises a means for combining the vehicle and agent into the final antiproliferative composition, e.g. a mixing adapter where the agent and vehicle are present in separate syringes.

The following examples are offered by way of illustration and not by way of limitation.

EXPERIMENTAL

I. Delivery Vehicles Studied for the Intralesional Administration of Anticellular Proliferative Agents

| Vehicle 17 (peanut oil/oleic acid gel) | |
|---|---|
| Ingredient | Content per mL |
| cytotoxic drug | (see Table 1) |
| oleic acid | 0.1 mL |
| aluminum monostearate | 48 mg |
| peanut oil | qs to 1 mL |

Six hundred mg of aluminum monostearate was dispersed in 10 mL of peanut oil and heated with stirring to 100–120° C. for 15 minutes, then cooled to room temperature. An 8 mL volume of this material was mixed with 1 mL of oleic acid via syringe-to-syringe transfer 30 times through a connecting Luer mixing adapter, to produce a bulk peanut oil/oleic acid gel. A solution or suspension of the cytotoxic drug in peanut oil was prepared by combining the appropriate weight of drug (see Table 1) with 1 mL of peanut oil and dispersing/dissolving by mixing vigorously and/or sonicating. Finally, 0.9 mL of bulk peanut oil/oleic acid gel was mixed with 0.1 mL of cytotoxic drug solution or suspension by syringe-to-syringe transfer 30 times through a connecting Luer mixing adaper to produce the final gel.

| Vehicle 18 (benzyl benzoate gel) | |
|---|---|
| Ingredient | Content per mL |
| cytotoxic drug | (see Table 1) |
| ethylcellulose | 40 mg |
| benzyl benzoate | qs to 1 mL |

A bulk benzyl benzoate gel was prepared by dispersing 400 mg of ethyl cellulose in 8.6 mL of benzyl benzoate and heating with occasional stirring to 37° C. for 24 hours, then cooling to room temperature. A solution or suspension of the cytotoxic drug in benzyl benzoate was prepared by combining the appropriate weight of drug (see Table 1) with 1 mL of benzyl benzoate and dispersing/dissolving by mixing vigorously and/or sonicating. Finally, 0.9 mL of bulk benzyl benzoate gel was mixed with 0.1 mL of cytotoxic drug solution or suspension by syringe-to-syringe transfer 30 times through a connecting Luer mixing adaper to produce the final gel.

| Vehicle 19 (polyethylene glycol 400 gel) | |
|---|---|
| Ingredient | Content per mL |
| cytotoxic drug | (see Table 1) |
| polyvinylpyrrolidone | 40 mg |
| polyethylene glycol 400 | qs to 1 mL |

A bulk polyethylene glycol gel was prepared by dispersing 400 mg of polyvinylpyrrolidone in 8.6 mL of polyethylene glycol 400 and heating with occasional stirring to 37° C. for 24 hours, then cooling to room temperature. A solution or suspension of the cytotoxic drug in polyethylene glycol was prepared by combining the appropriate weight of drug (see Table 1) with 1 mL of polyethylene glycol 400 and dispersing/dissolving by mixing vigorously and/or sonicating. Finally, 0.9 mL of bulk polyethylene glycol gel was mixed with 0.1 mL of cytotoxic drug solution or suspension by syringe-to-syringe transfer thirty times through a connecting Luer mixing adapter to produce the final gel.

| Vehicle 20 (ethanol/oleic acid gel) | |
|---|---|
| Ingredient | Content per mL |
| cytotoxic drug | (see Table 1) |
| oleic acid | 0.1 mL |
| hydroxypropyl cellulose | 30 mg |
| ethanol | qs to 1 mL |

Three hundred mg of hydroxypropyl cellulose was dispersed in 7.7 mL of ethanol and heated with occasional stirring to 37° C. for 24 hours, then cooled to room temperature. The resultant gel was mixed with 1 mL of oleic acid via syringe-to-syringe transfer 30 times through a connecting Luer mixing adapter to produce a bulk ethanol/oleic acid gel. A solution or suspension of the cytotoxic drug in ethanol was prepared by combining the appropriate weight of drug (see Table 1) with 1 mL of ethanol and dispersing/dissolving by mixing vigorously and/or sonicating. Finally, 0.9 mL of bulk ethanol/oleic acid gel was mixed with 0.1 mL of cytotoxic drug solution or suspension by syringe-to-syringe transfer 30 times through a connecting Luer mixing adaper to produce the final gel.

| Vehicle 21 (dimethylacetamide gel) | |
|---|---|
| Ingredient | Content per mL |
| cytotoxic drug | (see Table 1) |
| methylcellulose | 50 mg |
| dimethylacetamide | qs to 1 mL |

A bulk dimethylacetamide gel was prepared by dispersing 500 mg of methyl cellulose in 8.5 mL of dimethylacetamide and heating with occasional stirring to 37° C. for 24 hours, then cooling to room temperature. A solution or suspension of the cytotoxic drug in dimethylacetamide was prepared by combining the appropriate weight of drug (see Table 1) with 1 mL of dimethylacetamide and dispersing/dissolving by mixing vigorously and/or sonicating. Finally, 0.9 mL of bulk dimethylacetamide gel was mixed with 0.1 mL of cytotoxic drug solution or suspension by syringe-to-syringe transfer 30 times through a connecting Luer mixing adaper to produce the final gel.

Vehicle 22 (propylene carbonate gel)

| Ingredient | Content per mL |
| --- | --- |
| cytotoxic drug | (see Table 1) |
| polyvinylpyrrolidone | 100 mg |
| propylene carbonate | qs to 1 mL |

A bulk propylene carbonate gel was prepared by dispersing 1000 mg of polyvinylpyrrolidone in 8.0 mL of propylene carbonate and heating with occasional stirring to 37° C. for 24 hours, then cooling to room temperature. A solution or suspension of the cytotoxic drug in propylene carbonate was prepared by combining the appropriate weight of drug (see Table 1) with 1 mL of propylene carbonate and dispersing/dissolving by mixing vigorously and/or sonicating. Finally, 0.9 mL of bulk propylene carbonate gel was mixed with 0.1 mL of cytotoxic drug solution or suspension by syringe-to-syringe transfer 30 times through a connecting Luer mixing adaper to produce the final gel.

Vehicle 24 (dimethylacetamide/water/methylcellulose gel)

| Ingredient | Content per mL |
| --- | --- |
| cytotoxic drug | (see Table 1) |
| water | 0.1 mL |
| methylcellulose | 40 mg |
| dimethylacetamide | qs to 1 mL |

A bulk dimethylacetamide/water/methylcellulose gel was prepared by dispersing 400 mg of methyl cellulose in 7.6 mL of dimethylacetamide plus 1 mL water, stirring vigorously until dispersed, and heating to 121° C. for 1 hour, then cooling to room temperature. A solution or suspension of the cytotoxic drug in dimethylacetamide was prepared by combining the appropriate weight of drug (see Table 1) with 1 mL of dimethylacetamide and dispersing/dissolving by mixing vigorously and/or sonicating. Finally, 9 mL of bulk dimethylacetamide/water/methylcellulose gel was mixed with 1 mL of cytotoxic drug solution or suspension by syringe-to-syringe transfer 30 times through a connecting Luer mixing adapter to produce the final gel.

Vehicle 25 (dimethylacetamide/water/hydroxypropyl methylcellulose gel)

| Ingredient | Content per mL |
| --- | --- |
| cytotoxic drug | (see Table 1) |
| water | 0.1 mL |
| hydroxypropyl methylcellulose | 40 mg |
| dimethylacetamide | qs to 1 mL |

A bulk dimethylacetamide/water/hydroxypropyl methylcellulose gel was prepared by dispersing 2.4 g of hydroxypropyl methylcellulose in 40 mL of dimethylacetamide plus 6 mL water, stirring vigorously and heating to 90° C. until fully dispersed. The mixture was heated at 121° C. for 60 minutes, then cooled to room temperature. A solution or suspension of the cytotoxic drug in dimethylacetamide was prepared by combining the appropriate weight of drug (see Table 1) with 1 mL of dimethylacetamide and dispersing/dissolving by mixing vigorously and/or sonicating. Finally, 4 mL of bulk dimethylacetamide/ water/hydroxypropyl methylcellulose gel was mixed with 1 mL of cytotoxic drug solution/suspension by syringe-to-syringe transfer through a connecting Luer mixing adapter to produce the final gel.

Vehicle 26 (dimethylacetamide/water/carbomer (carboxypolymethylene) gel)

| Ingredient | Content per mL |
| --- | --- |
| cytotoxic drug | (see Table 1) |
| water | 0.1 mL |
| carbomer | 15 mg |
| dimethylacetamide | qs to 1 mL |

A dimethylacetamide/water/carbomer gel was prepared by first dispersing 150 mg of carbomer in 0.98 mL of water, allowing the stirred mixture to dissolve, and then stirring vigorously to achieve an aqueous gel concentrate. A solution or suspension of the cytotoxic drug dimethylacetamide was then prepared by combining the appropriate weight of drug (see Table 1) with 9 mL of dimethylacetamide and dispersing/dissolving by mixing vigorously and/or sonicating. Finally, 9 mL of the above dimethylacetamide solution was slowly added to 1 mL of the aqueous gel concentrate, with continuous stirring, to produce the final gel.

Vehicle 27 (dimethylacetamide/water/ethanol/carboxymethylcellulose gel)

| Ingredient | Content per mL |
| --- | --- |
| cytotoxic drug | (see Table 1) |
| water | 0.1 mL |
| ethanol | 0.1 mL |
| carboxymethylcellulose | 10 mg |
| dimethylacetamide | qs to 1 mL |

A dimethylacetamide/water/ethanol/ carboxymethylcellulose gel was prepared by first converting sodium carboxymethylcellulose into the carboxylic acid form by dispersing 4 g of sodium carboxymethylcellulose in 200 mL of water, and adjusting the pH to 2.0–2.5 using 1N HCl. Six hundred mL of ethanol was then slowly added, while stirring. The resultant carboxymethylcellulose precipitate was concentrated via centrifugation. A highly viscous aqueous/ethanolic gel concentrate was subsequently prepared by adding 1 mL of water to 1 g of the precipitate (containing 0.1 g of carboxymethylcellulose and 0.9 g of ethanol), and mixing under high shear until the mixture became clear. A solution or suspension of the cytotoxic drug in dimethylacetamide was separately prepared by combining the appropriate weight of drug (see Table 1) with 8 mL of dimethylacetamide and dispersing/dissolving by mixing vigorously and/or sonicating. Finally, 8 mL of the above dimethylacetamide solution was slowly added to 2 mL of the aqueous/ethanolic gel concentrate, with continuous high speed stirring, to produce the final gel.

| Vehicle 28 (carbomer/dimethyl sulfoxide (DMSO) gel) | | |
|---|---|---|
| Ingredient | mg/g | mg/g |
| camptothecin ("CPT") | 10.0 | — |
| carbomer, NF (Carbopol 974P) | 20 | 20 |
| water | 80 | 80 |
| DMSO | 900 | 900 |

Two grams of carbomer were dispersed in 40 g of DMSO. Eight grams of water were added with vigorous stirring, forming a viscous gel concentrate. Independently, 60 mg of camptothecin were suspended in 3 g of DMSO to produce a 20 mg/mL suspension. Equal weights of the gel concentrate and the camptothecin suspension (2.5 g each) were then mixed together to form the final 10 mg/g CPT gel. Placebo gel was prepared by mixing 2.5 g of gel concentrate with 2.5 g of DMSO. Gels containing CPT at 5, 2, and 1 mg/g were prepared by mixing appropriate portions of the 10 mg/g and placebo gels.

| Vehicles 29–31 (carbomer/DMSO/PEG 300 gel) | | | | | | |
|---|---|---|---|---|---|---|
| | Vehicle 29 | | Vehicle 30 | | Vehicle 31 | |
| Ingredient | mg/g | mg/g | mg/g | mg/g | mg/g | mg/g |
| camptothecin | 1.0 | — | 1.0 | — | 1.0 | — |
| carbomer, NF (Carbopol 974P) | 20 | — | 20 | — | 20 | — |
| water | 80 | 80 | 80 | 80 | 30 | 30 |
| PEG 300 | — | — | 500 | 500 | 800 | 800 |
| DMSO | 900 | 900 | 400 | 400 | 150 | 150 |

A stock solution of CPT was prepared by dissolving 32.8 mg of CPT in 4.93 g of DMSO. Stock gels were prepared by dispersing carbomer in DMSO, then adding water and PEG 300 as appropriate. Final CPT gels were made by mixing the appropriate volumes of CPT stock solution and stock gel. Final placebo gels were made by mixing the appropriate volumes of DMSO and stock gel.

| dimethylacetamide solution | |
|---|---|
| Ingredient | Content per mL |
| cytotoxic drug | (see Table 1) |
| dimethylacetamide | qs to 1 mL |

A solution was prepared by combining the appropriate weight of drug (see Table 1) with 1 mL of dimethylacetamide and dissolving by mixing vigorously.

| dimethylacetamide/water solution | |
|---|---|
| Ingredient | Content per mL |
| cytotoxic drug | (see Table 1) |
| water | 0.1 mL |
| dimethylacetamide | qs to 1 mL |

A solution was prepared by combining 1 mL of water with 9 mL of dimethylacetamide, mixing thoroughly, adding the appropriate weight of cytotoxic agent (see Table 1) to the mixture, and mixing vigorously until the drug dissolves.

In addition to the above organic solvent based vehicles being employed as delivery systems for cytotoxic agents in animal efficacy studies, the drugs were also administered as aqueous solutions or suspensions, or administered in a manner where the drug was dispersed/dissolved in an aqueous 2% collagen gel. The compositions of such water-based formulations are described below.

| aqueous solution | |
|---|---|
| Ingredient | Content per mL |
| cytotoxic drug | (see Table 1) |
| 0.9% sodium chloride solution | qs to 1 mL |

A solution was prepared by adding the appropriate weight of drug (see Table 1) to 1 mL of isotonic (0.9%) saline solution and dissolving by mixing vigorously.

| aqueous suspension | |
|---|---|
| Ingredient | Content per mL |
| cytotoxic drug | (see Table 1) |
| sodium carboxymethylcellulose | 5 mg |
| polysorbate 80 | 0.75 mg |
| water | qs to 1 mL |

A suspending vehicle was prepared by dispersing 50 mg of sodium carboxymethylcellulose and 7.5 mg of polysorbate 80 in 10 mL of water and stirring vigorously and/or sonicating until dissolved. The required amount of drug substance (see Table 1) was added directly to the resultant viscous solution and stirred vigorously and/or sonicated until uniformly dispersed.

| 2% collagen gel | |
|---|---|
| Ingredient | Content per mL |
| cytotoxic drug | (see Table 1) |
| purified bovine collagen | 20 mg |
| sodium phosphates | 30 mM |
| sodium chloride | 14 mM |
| water or suspending vehicle | qs to 1 mL |

Formulations of drugs in 2% collagen were prepared by adding the required amount of cytotoxic agent (see Table 1) to 2.0 mL of either water or suspending vehicle and stirring vigorously and/or sonicating until dissolved or dispersed. A 1.35-mL aliquot was then transferred into a syringe and mixed with 0.6 mL of 6.5% collagen gel by syringe-to-syringe transfer 30 times through a connecting Luer mixing adaper to produce the final gel.

Concentrations of the various cytotoxic drugs present in the above vehicles varied between the several studies performed. Specific concentrations employed are provided in the examples below. The range of drugs and concentrations employed during animal efficacy assessments of the above substantially non-aqueous delivery vehicles are presented in Table 1.

TABLE 1

Cytotoxic Agents and Concentrations Employed During Evaluation of Formulation Efficacy

| drug | concentration (mg/mL) |
|---|---|
| cisplatin | 1 or 2 |
| camptothecin | 0.25, 0.5, 1, 1.25, 2, 2.5, 5 or 10 |
| paclitaxel | 1 or 2 |
| vinblastine | 0.125 or 0.5 |
| fluorouracil | 3.75 or 15 |
| doxorubicin | 1.25 or 2.5 |
| etoposide | 5 or 10 |
| mitomycin | 1 or 2 |
| bleomycin | 1.25 or 2.5 |
| mechlorethamine | 0.025 or 0.05 |

Vehicle formulations 27–31, and particularly 28–31, are representative of the gelled polar organic solvent vehicles of the subject invention.

II. Testing Protocols

The following procedures were followed to study the delivery vehicle effect on the efficacy of various anticellular proliferative agents.

Transplantable syngeneic murine squamous cell carcinoma (SCCVII) or radiation-induced fibrosarcoma (RIF-1) tumors were grown intradermally in the flank of 3–7 month old female C3H mice ($2 \times 10^5$ cells were injected). When the introduced tumors reached 100 mm$^3$, the mice were ready for testing. During the course of the experiments, the treated and control tumors were measured three times per week with Vernier calipers and the tumor volumes were calculated using the following formula:

$$V = B/6 \times D_1 \times D_2 \times D_3$$

where $D_1$–$D_3$ are tumor diameters in millimeters. The number of days for tumors to reach four times (4x) their baseline volume was used as a parameter of treatment effectiveness and endpoint of the study. Therefore, a longer delay in tumor growth meant greater antitumor efficacy.

Transplantable mouse bladder tumors (MBT-2) were grown ectopically (intradermally) or orthotopically, and rat liver tumors (N1×S1) were grown orthotopically. Ectopic tumors were grown and analyzed as described above. Volumes of orthotopically grown tumors were determined using the formula described above, with volume measurements being performed on day 0 and again on either day 7 or day 8. The ratio of tumor volume at day 7–8 to tumor volume at start of treatment was used as a measure of treatment effectiveness. Therefore, a smaller ratio meant greater antitumor efficacy.

III. Evaluation of Agent Efficacy in Various Delivery Vehicles

The efficacy of ten different antiproliferative agents was evaluated in various substantially non-aqueous delivery vehicles, and compared with the efficacy of the agents in aqueous solution, suspension and aqueous collagen gel vehicles. The ten different agents evaluated were: cisplatin (CDDP), camptothecin (CPT), paclitaxel, vinblastine (VLB) fluorouracil (5-FU), doxorubicin (DXR), etoposide (VP-16), mitomycin (MTC), bleomycin, and mechlorethamine (HN2).

EXAMPLE 1

Effect of CDDP in Various Vehicles on SCCVII Tumor Growth

| Treatment Group | Conc/Dosage (mg/mL) | Conc/Dosage (mg/kg) | Route Inj. | Inj. Vol. (µL) | No. Tumors | 4X Tumor Growth (M ± SE in days) Treated | 4X Tumor Growth (M ± SE in days) Untreated |
|---|---|---|---|---|---|---|---|
| 1 untreated control | — | — | — | — | 10 | 5.7 ± 0.3 | |
| 2 CDDP solution | 1 | 4 | i.p. | 100 | 10 | 5.6 ± 0.1 | |
| 3 CDDP suspension | 2 | 4 | i.t. | 50 | 5, 5 | 11.3 ± 1.2 | 5.7 ± 0.2 |
| 4 CDDP in 2% collagen gel | 2 | 4 | i.t. | 50 | 5, 5 | 10.6 ± 1.1 | 6.1 ± 0.6 |
| 5 Vehicle 17 | — | — | i.t. | 50 | 5, 5 | 6.3 ± 0.8 | 4.6 ± 0.2 |
| 6 Vehicle 18 | — | — | i.t. | 50 | 5, 5 | 4.8 ± 0.2 | 4.5 ± 0.1 |
| 7 Vehicle 19 | — | — | i.t. | 50 | 5, 5 | 5.2 ± 0.5 | 4.9 ± 0.4 |
| 8 Vehicle 20 | — | — | i.t. | 50 | 5, 5 | 8.2 ± 1.2 | 4.9 ± 0.1 |
| 9 Vehicle 21 | — | — | i.t. | 50 | 5, 5 | 7.3 ± 0.9 | 5.7 ± 0.4 |
| 10 Vehicle 22 | — | — | i.t. | 50 | 5, 5 | 12.1 ± 1.7 | 4.9 ± 0.3 |
| 11 CDDP in Vehicle 17 | 2 | 4 | i.t. | 50 | 5, 5 | 9.2 ± 1.6 | 5.4 ± 0.3 |
| 12 CDDP in Vehicle 18 | 2 | 4 | i.t. | 50 | 5, 5 | 7.6 ± 0.7 | 5.4 ± 0.4 |
| 13 CDDP in Vehicle 19 | 2 | 4 | i.t. | 50 | 5, 5 | 7.0 ± 0.5 | 5.4 ± 0.4 |
| 14 CDDP in Vehicle 20 | 2 | 4 | i.t. | 50 | 5, 5 | 14.3 ± 4.0* | 5.4 ± 0.2 |
| 15 CDDP in Vehicle 21 | 2 | 4 | i.t. | 50 | 5, 5 | 14.9 ± 1.9 | 5.5 ± 0.4 |
| 16 CDDP in Vehicle 22 | 2 | 4 | i.t. | 50 | 4, 5 | 13.5 ± 2.4 | 4.7 ± 0.5 |

*one animal had no tumor present on day 30

EXAMPLE 2

Effect of Camptothecin (CPT) in Various Vehicles on SCCVII Tumor Growth

| Treatment Group | Conc/Dosage (mg/mL) | Conc/Dosage (mg/kg) | Route Inj. | Inj. Vol. (µL) | No. Tumors | 4X Tumor Growth (M ± SE in days) Treated | 4X Tumor Growth (M ± SE in days) Untreated |
|---|---|---|---|---|---|---|---|
| 1 untreated control | — | — | — | — | 10 | 4.1 ± 0.2 | |
| 2 CPT suspension | 1.25 | 5 | i.p. | 100 | 10 | 6.5 ± 0.2 | |
| 3 CPT in suspension | 2.5 | 5 | i.t. | 50 | 5, 5 | 6.0 ± 0.3 | 5.2 ± 0.4 |
| 4 CPT in 2% collagen gel | 2.5 | 5 | i.t. | 50 | 5, 5 | 6.1 ± 0.5 | 5.5 ± 0.1 |
| 5 camptothecin/Vehicle 17 | 2.5 | 5 | i.t. | 50 | 5, 5 | 7.0 ± 1.1 | 4.7 ± 0.4 |
| 6 camptothecin/Vehicle 18 | 2.5 | 5 | i.t. | 50 | 5, 5 | 6.1 ± 0.7 | 6.2 ± 0.5 |
| 7 camptothecin/Vehicle 19 | 2.5 | 5 | i.t. | 50 | 5, 5 | 6.8 ± 1.0 | 5.4 ± 0.4 |
| 8 camptothecin/Vehicle 20 | 2.5 | 5 | i.t. | 50 | 5, 5 | 11.3 ± 1.6 | 5.6 ± 0.7 |
| 9 camptothecin/Vehicle 21 | 2.5 | 5 | i.t. | 50 | 5, 5 | 16.0 ± 3.3 | 5.7 ± 0.4 |
| 10 camptothecin/Vehicle 22 | 2.5 | 5 | i.t. | 50 | 5, 5 | 8.9 ± 1.4 | 5.6 ± 0.4 |

EXAMPLE 3

Effect of Paclitaxel in Various Vehicles on SCCVII Tumor Growth

| Treatment Group | Conc/Dosage (mg/mL) | Conc/Dosage (mg/kg) | Route Inj. | Inj. Vol. (µL) | No. Tumors | 4X Tumor Growth (M ± SE in days) Treated | 4X Tumor Growth (M ± SE in days) Untreated |
|---|---|---|---|---|---|---|---|
| 11 paclitaxel solution | 1 | 4 | i.p. | 100 | 2 | 5.3 ± 0.1 | |
| 12 paclitaxel solution | 2 | 4 | i.t. | 50 | 5, 5 | 4.9 ± 0.2 | 4.6 ± 0.3 |
| 13 pac. in 2% collagen gel | 2 | 4 | i.t. | 50 | 5, 5 | 4.1 ± 0.3 | 4.6 ± 0.1 |
| 14 paclitaxel/Vehicle 17 | 2 | 4 | i.t. | 50 | 5, 5 | 5.2 ± 0.2 | 5.1 ± 0.2 |
| 15 paclitaxel/Vehicle 18 | 2 | 4 | i.t. | 50 | 5, 5 | 5.8 ± 0.3 | 4.5 ± 0.3 |
| 16 paclitaxel/Vehicle 19 | 2 | 4 | i.t. | 50 | 5, 5 | 4.9 ± 0.2 | 4.7 ± 0.2 |
| 17 paclitaxel/Vehicle 20 | 2 | 4 | i.t. | 50 | 5, 5 | 5.8 ± 0.7 | 4.7 ± 0.4 |
| 18 paclitaxel/Vehicle 21 | 2 | 4 | i.t. | 50 | 5, 5 | 7.8 ± 0.9 | 4.8 ± 0.3 |
| 19 paclitaxel/Vehicle 22 | 2 | 4 | i.t. | 50 | 5, 5 | 8.2 ± 1.7 | 4.2 ± 0.2 |

EXAMPLE 4

Effect of Vinblastine (VLB) in Various Vehicles on SCCVII Tumor Growth

| Treatment Group | Conc/Dosage (mg/mL) | Conc/Dosage (mg/kg) | Route Inj. | Inj. Vol. (µL) | No. Tumors | 4X Tumor Growth (M ± SE in days) Treated | 4X Tumor Growth (M ± SE in days) Untreated | No. Cure |
|---|---|---|---|---|---|---|---|---|
| 1 untreated control | — | — | — | — | 10 | 5.2 ± 0.3 | | |
| 2 VLB solution | 0.125 | 1 | i.p. | 200 | 10 | 5.6 ± 0.2 | | |
| 3 VLB solution | 0.5 | 1 | i.t. | 50 | 5, 5 | 7.8 ± 0.3 | 6.5 ± 0.5 | — |
| 4 VLB in 2% collagen gel | 0.5 | 1 | i.t. | 50 | 5, 5 | 9.9 ± 1.1 | 5.8 ± 0.3 | — |
| 5 Vehicle 17 | — | — | i.t. | 50 | 5, 5 | 6.1 ± 0.5 | 5.6 ± 0.5 | — |
| 6 Vehicle 18 | — | — | i.t. | 50 | 5, 5 | 7.5 ± 1.1 | 5.8 ± 0.3 | — |
| 7 Vehicle 19 | — | — | i.t. | 50 | 5, 5 | 6.0 ± 0.2 | 5.6 ± 0.4 | — |
| 8 Vehicle 20 | — | — | i.t. | 50 | 5, 5 | 9.5 ± 1.5 | 5.8 ± 0.5 | — |
| 9 Vehicle 21 | — | — | i.t. | 50 | 5, 5 | 7.7 ± 0.7 | 6.1 ± 0.1 | — |
| 10 Vehicle 22 | — | — | i.t. | 50 | 5, 5 | 9.2 ± 1.2 | 6.2 ± 0.4 | — |
| 11 VLB in Vehicle 17 | 0.5 | 1 | i.t. | 50 | 5, 5 | 6.5 ± 0.2 | 5.4 ± 0.5 | — |
| 12 VLB in Vehicle 18 | 0.5 | 1 | i.t. | 50 | 5, 5 | 6.8 ± 0.4 | 5.3 ± 0.4 | — |
| 13 VLB in Vehicle 19 | 0.5 | 1 | i.t. | 50 | 5, 5 | 6.9 ± 0.4 | 5.4 ± 0.3 | — |
| 14 VLB in Vehicle 20 | 0.5 | 1 | i.t. | 50 | 5, 5 | 12.4 ± 2.2 | 5.4 ± 0.5 | — |
| 15 VLB in Vehicle 21 | 0.5 | 1 | i.t. | 50 | 5, 5 | 18.7 ± 3.9 | 6.3 ± 0.2 | 1 |
| 16 VLB in Vehicle 22 | 0.5 | 1 | i.t. | 50 | 5, 5 | 13.7 ± 1.2 | 5.9 ± 0.3 | — |

EXAMPLE 5

Effect of 5-FU in Various Vehicles on SCCVII Tumor Growth

| Treatment Group | Conc/Dosage (mg/mL) | Conc/Dosage (mg/kg) | Route Inj. | Inj. Vol. (μL) | No. Tumors | 4X Tumor Growth (M ± SE in days) Treated | 4X Tumor Growth (M ± SE in days) Untreated |
|---|---|---|---|---|---|---|---|
| 1 untreated control | — | — | — | — | 10 | 5.1 ± 0.3 | |
| 2 5-FU solution | 3.75 | 30 | i.p. | 200 | 10 | 7.4 ± 0.2 | |
| 3 5-FU solution | 15 | 30 | i.t. | 50 | 5, 5 | 11.1 ± 0.7 | 8.6 ± 0.3 |
| 4 5-FU in 2% collagen gel | 15 | 30 | i.t. | 50 | 5, 5 | 14.8 ± 0.5 | 8.4 ± 0.2 |
| 5 Vehicle 17 | — | — | i.t. | 50 | 5, 5 | 6.3 ± 0.5 | 4.7 ± 0.3 |
| 6 Vehicle 18 | — | — | i.t. | 50 | 5, 5 | 6.4 ± 0.4 | 5.2 ± 0.5 |
| 7 Vehicle 19 | — | — | i.t. | 50 | 5, 5 | 5.2 ± 0.5 | 4.4 ± 0.3 |
| 8 Vehicle 20 | — | — | i.t. | 50 | 5, 5 | 6.2 ± 0.7 | 4.6 ± 0.2 |
| 9 Vehicle 21 | — | — | i.t. | 50 | 5, 5 | 8.3 ± 0.5 | 6.0 ± 0.5 |
| 10 Vehicle 22 | — | — | i.t. | 50 | 5, 5 | 9.4 ± 1.8 | 4.8 ± 0.3 |
| 11 5-FU in Vehicle 17 | 15 | 30 | i.t. | 50 | 5, 5 | 12.1 ± 1.1 | 6.7 ± 0.3 |
| 12 5-FU in Vehicle 18 | 15 | 30 | i.t. | 50 | 5, 5 | 11.4 ± 1.5 | 7.0 ± 0.3 |
| 13 5-FU in Vehicle 19 | 15 | 30 | i.t. | 50 | 5, 5 | 12.0 ± 0.7 | 7.4 ± 0.5 |
| 14 5-FU in Vehicle 20 | 15 | 30 | i.t. | 50 | 5, 5 | 18.3 ± 1.2 | 8.2 ± 0.9 |
| 15 5-FU in Vehicle 21 | 15 | 30 | i.t. | 50 | 5, 5 | 17.1 ± 1.5 | 7.9 ± 0.5 |
| 16 5-FU in Vehicle 22 | 15 | 30 | i.t. | 50 | 5, 5 | >15.5 ± 1.4 | 6.8 ± 0.2 |

EXAMPLES 6 & 7

Effect of Bleomycin (4 mg/kg) and Doxorubicin (20 mg/kg) in Various Vehicles on SCCVII Tumor Growth

| Treatment Group | Conc/Dosage (mg/mL) | Conc/Dosage (mg/kg) | Route Inj. | Inj. Vol. (μL) | No. Tumors | 4X Tumor Growth (M ± SE in days) Treated | 4X Tumor Growth (M ± SE in days) Untreated |
|---|---|---|---|---|---|---|---|
| Example 6 | | | | | | | |
| 1 untreated control | — | — | — | — | 10 | 5.2 ± 0.2 | |
| 2 bleomycin suspension | 1.25 | 5 | i.p. | 100 | 10 | 5.5 ± 0.3 | |
| 3 bleomycin suspension | 2.5 | 5 | i.t. | 50 | 5, 5 | 6.9 ± 0.5 | 5.0 ± 0.5 |
| 4 bleomycin in 2% collagen | 2.5 | 5 | i.t. | 50 | 5, 5 | 6.4 ± 0.5 | 5.8 ± 0.5 |
| 5 bleomycin/Vehicle 17 | 2.5 | 5 | i.t. | 50 | 5, 5 | 6.2 ± 0.5 | 5.2 ± 0.4 |
| 6 bleomycin/Vehicle 18 | 2.5 | 5 | i.t. | 50 | 5, 5 | 7.5 ± 0.8 | 5.7 ± 0.4 |
| 7 bleomycin/Vehicle 19 | 2.5 | 5 | i.t. | 50 | 5, 5 | 8.0 ± 0.2 | 5.3 ± 0.2 |
| 8 bleomycin/Vehicle 20 | 2.5 | 5 | i.t. | 50 | 5, 5 | 11.5 ± 0.4 | 6.1 ± 0.2 |
| 9 bleomycin/Vehicle 21 | 2.5 | 5 | i.t. | 50 | 5, 5 | 10.5 ± 0.8 | 5.9 ± 0.5 |
| 10 bleomycin/Vehicle 22 | 2.5 | 5 | i.t. | 50 | 5, 5 | 12.1 ± 0.6 | 6.1 ± 0.5 |
| Example 7 | | | | | | | |
| 11 doxorubicin solution | 1.25 | 5 | i.p. | 100 | 10 | 5.5 ± 0.3 | |
| 12 doxorubicin solution | 15 | 30 | i.t. | 50 | 5, 5 | 10.2 ± 0.7 | 5.9 ± 0.3 |
| 13 doxorubicin in 2% collagen | 15 | 30 | i.t. | 50 | 5, 5 | 8.5 ± 1.2 | 5.4 ± 0.2 |
| 14 doxorubicin in Veh. 17 | 15 | 30 | i.t. | 50 | 5, 5 | 6.7 ± 0.7 | 5.2 ± 0.2 |
| 15 doxorubicin in Veh. 18 | 15 | 30 | i.t. | 50 | 5, 5 | 6.4 ± 0.8 | 5.1 ± 0.3 |
| 16 doxorubicin in Veh. 19 | 15 | 30 | i.t. | 50 | 5, 5 | 8.8 ± 1.5 | 5.4 ± 0.4 |
| 17 doxorubicin in Veh. 20 | 15 | 30 | i.t. | 50 | 5, 5 | 11.0 ± 1.4 | 6.0 ± 0.4 |
| 18 doxorubicin in Veh. 21 | 15 | 30 | i.t. | 50 | 5, 5 | 13.4 ± 3.0 | 5.9 ± 0.5 |
| 19 doxorubicin in Veh. 22 | 15 | 30 | i.t. | 50 | 5, 5 | 7.9 ± 0.7 | 5.6 ± 0.4 |

EXAMPLE 8

Effect of Mechlorethamine in Various Vehicles on SCCVII Tumor Growth

| Treatment Group | Conc/Dosage (mg/mL) | Conc/Dosage (mg/kg) | Route Inj. | Inj. Vol. (μL) | No. Tumors | 4X Tumor Growth (M ± SE in days) Treated | 4X Tumor Growth (M ± SE in days) Untreated |
|---|---|---|---|---|---|---|---|
| 1 untreated control | — | — | — | — | 10 | 5.8 ± 0.4 | |
| 2 mechlorethamine HCl | 0.025 | 0.1 | i.p. | 100 | 10 | 5.2 ± 0.2 | |
| 3 mechlorethanmine HCl | 0.05 | 0.1 | i.t. | 50 | 5, 5 | 5.7 ± 0.3 | 5.1 ± 0.6 |
| 4 mechlorethamine HCl in 2% collagen | 0.05 | 0.1 | i.t. | 50 | 5, 5 | 6.4 ± 0.6 | 5.1 ± 0.3 |
| 5 mechlorethamine HCl Vehicle 17 | 0.05 | 0.1 | i.t. | 50 | 5, 5 | 7.4 ± 1.4 | 6.3 ± 0.5 |
| 6 mechlorethamine HCl Vehicle 18 | 0.05 | 0.1 | i.t. | 50 | 5, 5 | 6.2 ± 0.9 | 5.7 ± 0.4 |
| 7 mechlorethamine HCl Vehicle 19 | 0.05 | 0.1 | i.t. | 50 | 5, 5 | 7.3 ± 1.1 | 5.2 ± 0.3 |
| 8 mechlorethamine HCl Vehicle 20 | 0.5 | 0.1 | i.t. | 50 | 5, 5 | 8.3 ± 1.3 | 5.3 ± 0.4 |
| 9 mechlorethamine HCl Vehicle 21 | 0.05 | 0.1 | i.t. | 50 | 5, 5 | 8.0 ± 1.0 | 4.9 ± 0.4 |
| 10 mechlorethamine HCl Vehicle 22 | 0.05 | 0.1 | i.t. | 50 | 5, 5 | 11.1 ± 1.7 | 5.4 ± 0.6 |

EXAMPLES 9 & 10

Effect of Mitomycin and Etoposide in Various Vehicles on SCCVII Tumor Growth

| Treatment Group | Conc/Dosage (mg/mL) | Conc/Dosage (mg/kg) | Route Inj. | Inj. Vol. (μL) | No. Tumors | 4X Tumor Growth (M ± SE in days) Treated | 4X Tumor Growth (M ± SE in days) Untreated |
|---|---|---|---|---|---|---|---|
| Example 9 | | | | | | | |
| 1 untreated control | — | — | — | — | 10 | 5.0 ± 0.2 | |
| 2 mitomycin suspension | 1 | 4 | i.p. | 100 | 10 | 5.9 ± 0.5 | |
| 3 mitomycin suspension | 1 | 4 | i.t. | 50 | 5, 5 | 6.2 ± 0.5 | 5.7 ± 0.3 |
| 4 mitomycin in 2% collagen | 1 | 4 | i.t. | 50 | 5, 5 | 6.9 ± 0.4 | 5.0 ± 0.4 |
| 5 mitomycin Vehicle 17 | 2 | 4 | i.t. | 50 | 5, 5 | 5.7 ± 0.6 | 5.1 ± 0.4 |
| 6 mitomycin Vehicle 18 | 2 | 4 | i.t. | 50 | 5, 5 | 8.0 ± 1.9 | 5.6 ± 0.3 |
| 7 mitomycin Vehicle 19 | 2 | 4 | i.t. | 50 | 5, 5 | 5.6 ± 0.1 | 4.8 ± 0.3 |
| 8 mitomycin Vehicle 20 | 2 | 4 | i.t. | 50 | 5, 5 | 10.5 ± 2.1 | 5.2 ± 0.4 |
| 9 mitomycin Vehicle 21 | 2 | 4 | i.t. | 50 | 5, 5 | 7.4 ± 0.5 | 6.5 ± 0.6 |
| 10 mitomycin Vehicle 22 | 2 | 4 | i.t. | 50 | 5, 5 | 11.5 ± 1.5 | 8.0 ± 0.5 |
| Example 10 | | | | | | | |
| 11 etoposide solution | 5 | 20 | i.p. | 100 | 10 | 5.0 ± 0.2 | |
| 12 etoposide solution | 10 | 20 | i.t. | 50 | 5, 5 | 5.8 ± 0.7 | 4.4 ± 0.2 |
| 13 etoposide in 2% collagen | 10 | 20 | i.t. | 50 | 5, 5 | 4.9 ± 0.2 | 5.2 ± 0.2 |
| 14 etoposide vehicle 17 | 10 | 20 | i.t. | 50 | 5, 5 | 5.2 ± 0.2 | 4.8 ± 0.2 |
| 15 etoposide Vehicle 18 | 10 | 20 | i.t. | 50 | 5, 5 | 4.8 ± 0.1 | 4.6 ± 0.1 |
| 16 etoposide Vehicle 19 | 10 | 20 | i.t. | 50 | 5, 5 | 4.7 ± 0.5 | 4.7 ± 0.1 |
| 17 etoposide Vehicle 20 | 10 | 20 | i.t. | 50 | 5, 5 | 6.4 ± 0.7 | 4.5 ± 0.3 |
| 18 etoposide Vehicle 21 | 10 | 20 | i.t. | 50 | 5, 5 | 10.0 ± 1.6 | 5.8 ± 0.3 |
| 19 etoposide Vehicle 22 | 10 | 20 | i.t. | 50 | 5, 5 | 5.8 ± 0.5 | 4.9 ± 0.2 |

It is evident from the above results and discussion that use of substantially non-aqueous, polar gel formulations according to the subject invention as delivery vehicles in the regional or local administration of antiproliferative agents results in enhanced agent efficacy. Specifically, use of the subject delivery vehicles for the delivery of antiproliferative agents provides for greater delays in lesion growth progression than does the delivery of the same antiproliferative agents in predominantly aqueous vehicles or non-polar aqueous vehicles.

EXAMPLE 11

Dose Response of Camptothecin (CPT) in Various Vehicles on RIF-1 Tumor Growth

| Treatment Group | Conc/Dosage (mg/mL) | Conc/Dosage (mg/kg) | Inj. Site | Inj. Vol. (μL) | No. Tumors | 4X Tumor Growth (M ± SE in days) Treated | 4X Tumor Growth (M ± SE in days) Untreated |
|---|---|---|---|---|---|---|---|
| 1 untreated control | — | — | — | — | 10 | 5.8 ± 0.2 | |
| 2 CPT aqueous suspension | 0.5 | 2 | i.p. | 100 | 10 | 7.3 ± 0.3 | |
| 3 CPT aqueous suspension | 1.25 | 5 | i.p. | 100 | 10 | 7.9 ± 0.3 | |
| 4 CPT aqueous suspension | 2.5 | 10 | i.p. | 100 | 10 | 9.8 ± 0.5 | |
| 5 CPT aqueous suspension | 5 | 20 | i.p. | 100 | 10 | 10.5 ± 0.8 | |
| 6 CPT aqueous suspension | 10 | 40 | i.p. | 100 | 10 | 12.8 ± 0.7 | |
| 7 CPT aqueous suspension | 0.5 | 1 | i.t. | 50 | 5, 5 | 8.5 ± 0.8 | 6.7 ± 0.3 |
| 8 CPT aqueous suspension | 1 | 2 | i.t. | 50 | 5, 5 | 7.3 ± 0.7 | 6.3 ± 0.4 |
| 9 CPT aqueous suspension | 2.5 | 5 | i.t. | 50 | 5, 5 | 8.1 ± 0.9 | 6.4 ± 0.4 |
| 10 CPT aqueous suspension | 5 | 10 | i.t. | 50 | 5, 5 | 8.8 ± 0.9 | 7.3 ± 0.7 |
| 11 CPT aqueous suspension | 10 | 20 | i.t. | 50 | 5, 5 | 16.3 ± 3.2 | 0.9 ± 0.7 |
| 12 DMA control | — | — | i.t. | 50 | 5, 5 | 10.1 ± 0.4 | 6.5 ± 0.2 |
| 13 CPT solution/DMA | 0.25 | 0.5 | i.t. | 50 | 5, 5 | 7.3 ± 0.2 | 7.1 ± 0.2 |
| 14 CPT solution/DMA | 0.5 | 1 | i.t. | 50 | 5, 5 | 9.3 ± 0.7 | 6.7 ± 0.3 |
| 15 CPT solution/DMA | 1 | 2 | i.t. | 50 | 5, 5 | 8.3 ± 0.4 | 7.4 ± 0.3 |
| 16 CPT solution/DMA | 2.5 | 5 | i.t. | 50 | 5, 5 | 13.3 ± 1.1 | 8.4 ± 0.3 |
| 17 CPT solution/DMA | 5 | 10 | i.t. | 50 | 5, 5 | 13.8 ± 1.8 | 9.9 ± 1.1 |
| 18 CPT/dipiv/DMA | 1 | 2 | i.t. | 50 | 5, 5 | 12.7 ± 0.8 | 7.8 ± 0.3 |
| 19 CPT/Vehicle 21 | 1 | 2 | i.t. | 50 | 5, 5 | 15.4 ± 2.4 | 8.0 ± 0.2 |
| 20 CPT/dipiv/Vehicle 21 | 1 | 2 | i.t. | 50 | 5, 5 | 14.2 ± 0.6 | 8.2 ± 0.2 |

EXAMPLE 12

Antitumor Effect of Camptothecin (CPT) in Various Vehicles on Orthotopic MBT-2 Bladder Tumors in Mice

| Treatment Group | Drug Conc. (mg/mL) | Drug Dose (mg/kg) | Inj. Site | Inj. Vol. (μL) | No. Tumors | Tumor Volume (mm³) day 0 | Tumor Volume (mm³) day 8 | Ratio (D-8/D-0) |
|---|---|---|---|---|---|---|---|---|
| 1 untreated control | — | — | — | — | 5 | 48 | died d-5 | — |
| | | | | | | 70 | 683 | 9.8 |
| | | | | | | 35 | 560 | 16.0 |
| | | | | | | 46 | 565 | 12.3 |
| | | | | | | 52 | 561 | 10.8 |
| | | | | | mean | 51 | 592 | 11.6/12.2 |
| 2 DMA | — | — | i.t. | 25 | 5 | 63 | 522 | 8.3 |
| | | | | | | 55 | 752 | 13.7 |
| | | | | | | 36 | 392 | 10.9 |
| | | | | | | 64 | 653 | 10.2 |
| | | | | | | 46 | 452 | 9.8 |
| | | | | | mean | 53 | 554 | 10.5/10.6 |
| 3 DMA gel (Vehicle 21) | — | — | i.t. | 25 | 5 | 62 | 485 | 7.8 |
| | | | | | | 61 | 575 | 9.4 |
| | | | | | | 39 | 176 | 4.5 |
| | | | | | | 46 | 545 | 11.8 |
| | | | | | | 66 | 716 | 10.8 |
| | | | | | mean | 55 | 499 | 9.1/8.9 |
| 4 CPT suspension | 0.5 | 2 | i.p. | 100 | 5 | 57 | died d-6 | — |
| | | | | | | 45 | 492 | 10.9 |
| | | | | | | 51 | 502 | 9.8 |
| | | | | | | 71 | 334 | 4.7 |
| | | | | | | 48 | 312 | 6.5 |
| | | | | | mean | 54 | 410 | 7.6/8.0 |
| 5 CPT suspension | 2 | 2 | i.t. | 25 | 6 | 62 | 492 | 7.9 |
| | | | | | | 42 | 351 | 8.4 |
| | | | | | | 57 | 324 | 5.7 |
| | | | | | | 53 | 492 | 9.3 |
| | | | | | | 63 | 365 | 5.8 |
| | | | | | | 36 | 432 | 12.0 |
| | | | | | mean | 52 | 409 | 7.9/8.2 |
| 3 CPT in DMA gel | 2 | 2 | i.t. | 25 | 6 | 54 | 302 | 5.6 |

-continued

Antitumor Effect of Camptothecin (CPT) in
Various Vehicles on Orthotopic MBT-2 Bladder Tumors in Mice

| Treatment Group | Drug Conc. (mg/mL) | Drug Dose (mg/kg) | Inj. Site | Inj. Vol. (µL) | No. Tumors | Tumor Volume (mm$^3$) day 0 | day 8 | Ratio (D-8/D-0) |
|---|---|---|---|---|---|---|---|---|
| (Vehicle 21) | | | | | | 68 | 205 | 3.0 |
| | | | | | | 36 | 98 | 2.7 |
| | | | | | | 43 | died d-5 | — |
| | | | | | | 43 | 77 | 1.8 |
| | | | | | | 61 | 78 | 1.3 |
| | | | | | mean | 52 | 152 | 2.9/2.9 |
| 7 CPT in DMA | 2 | 2 | i.t. | 25 | 6 | 47 | 356 | 7.6 |
| | | | | | | 63 | 356 | 5.7 |
| | | | | | | 63 | 477 | 7.6 |
| | | | | | | 41 | 375 | 10.1 |
| | | | | | | 37 | 375 | 6.5 |
| | | | | | | 56 | 427 | 7.6 |
| | | | | | mean | 51 | 376 | 7.4/7.5 |

EXAMPLE 13

Antitumor Effect of Camptothecin (CPT) in Various Vehicles
on Orthotopic N1-S1 Liver Tumors in Rats

| Treatment Group | Drug Conc. (mg/mL) | Drug Dose (mg/kg) | Inj. Site | Inj. Vol. (µL) | No. day 0 | Tumor Volume (mm$^3$) day 0 | day 8 | Ratio (D-8/D-0) | Note* |
|---|---|---|---|---|---|---|---|---|---|
| 1 untreated control | — | — | — | — | 3 | 104 | 1913 | 18.4 | |
| | | | | | | 82 | 1465 | 17.9 | |
| | | | | | | 95 | 1038 | 10.9 | |
| | | | | | mean | 94 | 1472 | 15.7/15.7 | |
| 2 DMA | — | — | i.t. | 100 | 3 | 97 | 721 | 7.4 | p |
| | | | | | | 119 | 1531 | 12.9 | p+ |
| | | | | | | 88 | 837 | 9.5 | p |
| | | | | | mean | 101 | 1030 | 10.2/9.9 | |
| 3 DMA gel (Vehicle 21) | — | — | i.t. | 100 | 2 | 117 | 2119 | 18.1 | p |
| | | | | | | 95 | 1945 | 20.5 | p |
| | | | | | mean | 106 | 2032 | 19.2/19.3 | |
| 4 CPT suspension | 0.5 | 0.5 | i.p. | 400 | 3 | 91 | 1280 | 14.1 | |
| | | | | | | 81 | 907 | 11.2 | |
| | | | | | | 92 | 2227 | 24.2 | |
| | | | | | mean | 88 | 1471 | 16.7/16.5 | |
| 5 CPT suspension | 2 | 0.5 | i.t. | 100 | 3 | 94 | 499 | 5.3 | |
| | | | | | | 90 | 451 | 5.0 | |
| | | | | | | 99 | 1514 | 15.3 | |
| | | | | | mean | 94 | 821 | 8.7/8.5 | |
| 6 CPT in DMA gel (Vehicle 21) | 2 | 0.5 | i.t. | 100 | 2 | 93 | 108 | 1.2 | |
| | | | | | | 99 | 280 | 2.8 | |
| | | | | | mean | 96 | 194 | 2.0/2.0 | |
| | | | | | 2 | 94 | 2212 | 23.5 | p |
| | | | | | | 117 | 3486 | 29.8 | p |
| | | | | | mean | 106 | 2849 | 26.9/26.7 | |
| 7 CPT in DMA | 2 | 0.5 | i.t. | 100 | 4 | 97 | 199 | 2.1 | |
| | | | | | | 105 | 741 | 7.1 | |
| | | | | | | 95 | 534 | 5.6 | |
| | | | | | | 105 | 276 | 2.6 | |
| | | | | | mean | 101 | 438 | 4.3/4.4 | |

Note*
tumor popped or broke open during intratumoral drug injection.

EXAMPLE 14

Antitumor Effect of Camptothecin (CPT) in Various Vehicles on Orthotopic MBT-2 Bladder Tumors in Mice

| Treatment Group | Drug Conc. (mg/mL) | Drug Dose (mg/kg) | Inj. Site | Inj. Vol. (µL) | No. Tumors | Tumor Volume (mm³) day 0 | Tumor Volume (mm³) day 8 | Ratio (D-8/D-0) |
|---|---|---|---|---|---|---|---|---|
| 1 untreated control | — | — | — | — | 4 | 70 | 594 | 8.5 |
| | | | | | | 63 | 580 | 9.2 |
| | | | | | | 53 | 612 | 11.5 |
| | | | | | | 33 | 404 | 12.2 |
| | | | | | mean | 54 | 595 | 11.0/10.4 |
| 2 Vehicle 21 | — | — | i.t. | 25 | 7 | 66 | 526 | 8.0 |
| | | | | | | 60 | 358 | 6.0 |
| | | | | | | 50 | 396 | 7.9 |
| | | | | | | 63 | 400 | 6.3 |
| | | | | | | 27 | 145 | 5.4 |
| | | | | | | 85 | 431 | 5.1 |
| | | | | | | 81 | 407 | 5.0 |
| | | | | | mean | 62 | 380 | 6.1/6.2 |
| 3 CPT suspension | 1.25 | 5 | i.p. | 100 | 5 | 70 | 365 | 5.2 |
| | | | | | | 49 | 325 | 6.6 |
| | | | | | | 47 | 95 | 2.0 |
| | | | | | | 66 | 130 | 2.0 |
| | | | | | | 33 | 110 | 3.3 |
| | | | | | mean | 53 | 205 | 3.9/3.8 |
| 4 CPT suspension | 5 | 5 | i.t. | 25 | 7 | 49 | 146 | 3.0 |
| | | | | | | 30 | 114 | 3.8 |
| | | | | | | 61 | 200 | 3.3 |
| | | | | | | 70 | 217 | 3.1 |
| | | | | | | 53 | 111 | 2.1 |
| | | | | | | 82 | 188 | 2.3 |
| | | | | | | 20 | 148 | 7.4 |
| | | | | | mean | 52 | 161 | 3.1/3.6 |
| 5 CPT Vehicle 21 | 5 | 5 | i.t. | 25 | 7 | 60 | 39 | 0.65 |
| | | | | | | 52 | 79 | 1.52 |
| | | | | | | 47 | 43 | 0.91 |
| | | | | | | 55 | 32 | 0.58 |
| | | | | | | 41 | 40 | 0.98 |
| | | | | | | 30 | 19 | 0.63 |
| | | | | | | 92 | 157 | 1.71 |
| | | | | | mean | 54 | 58 | 1.1/1.0 |

EXAMPLE 15

Ectopic Antitumor Effect of Camptothecin (CPT) in Various Vehicles on Mouse Bladder Tumors (MBT) in Mice

| Treatment Group | Drug Conc. (mg/mL) | Drug Dose (mg/kg) | Inj. Site | Inj. Vol. (µL) | No. Tumors | 4X Tumor Growth (M ± SE in days) Treated | 4X Tumor Growth (M ± SE in days) Untreated |
|---|---|---|---|---|---|---|---|
| 1 untreated control | — | — | — | — | 12 | 7.0 ± 0.3 | |
| 2 CPT suspension | 1.25 | 5 | i.p. | 100 | 12 | 8.0 ± 0.4 | |
| 3 CPT suspension | 2.5 | 5 | i.t. | 50 | 6 | 14.3 ± 1.0 | 8.1 ± 0.3 |
| 4 CPT in Vehicle 21 (DMA gel) | 2.5 | 5 | i.t. | 50 | 6 | 25.8 ± 1.2 | 8.0 ± 0.5 |

Group 4 One animal was found dead on Day 22 and Day 27 each, another one had no tumor present on Day 30.

EXAMPLE 16

Dose Response of Camptothecin in Various Vehicles on SCCVII Tumor Growth

| | Treatment Group | Drug Conc. (mg/mL) | Drug Dose (mg/kg) | Inj. Site Inj. | Inj. Vol. (µL) | No. Tumors | 4X Tumor Growth (M ± SE in days) Treated | Untreated |
|---|---|---|---|---|---|---|---|---|
| 1 | untreated control | — | — | — | — | 8 | 4.3 ± 0.1 | |
| 2 | CPT suspension | 1.25 | 5 | i.p. | 100 | 10 | 8.2 ± 0.3 | |
| 3 | CPT suspension | 2.5 | 10 | i.p. | 100 | 10 | 11.0 ± 0.6 | |
| 4 | CPT suspension | 5 | 20 | i.p. | 100 | 10 | 12.5 ± 1.3 | |
| 5 | CPT suspension | 1 | 2 | i.t. | 50 | 5,5 | 8.6 ± 0.8 | 5.9 ± 0.5 |
| 6 | CPT suspension | 2.5 | 5 | i.t. | 50 | 5,5 | 9.4 ± 0.4 | 7.0 ± 0.4 |
| 7 | CPT suspension | 5 | 10 | i.t. | 50 | 5,5 | 10.7 ± 0.9 | 8.5 ± 0.6 |
| 8 | CPT suspension | 10 | 20 | i.t. | 50 | 5,5 | 15.0 ± 2.6 | 9.1 ± 0.5 |
| 9 | DMT/water (solvent control) | — | — | i.t. | 50 | 5,5 | 9.3 ± 0.3 | 5.3 ± 0.3 |
| 10 | Vehicle 24 (placebo control) | — | — | i.t. | 50 | 5,5 | 9.4 ± 0.7 | 4.6 ± 0.4 |
| 11 | CPT solution in DMA/water | 0.5 | 1 | i.t. | 50 | 5,5 | 7.6 ± 1.2 | 5.7 ± 0.6 |
| 12 | CPT solution in DMA/water | 1 | 2 | i.t. | 50 | 5,5 | 7.8 ± 0.9 | 4.7 ± 0.5 |
| 13 | CPT solution in DMA/water | 2.5 | 5 | i.t. | 50 | 5,5 | 15.4 ± 2.8 | 5.8 ± 0.8 |
| 14 | CPT solution in DMA/water | 5 | 10 | i.t. | 50 | 5,5 | 10.9 ± 0.5 | 6.8 ± 0.5 |
| 15 | CPT in Vehicle 24 | 0.5 | 1 | i.t. | 50 | 5,5 | 10.1 ± 0.8 | 6.3 ± 0.4 |
| 16 | CPT in Vehicle 24 | 1 | 2 | i.t. | 50 | 5,5 | 14.2 ± 1.5 | 6.1 ± 0.7 |
| 17 | CPT in Vehicle 24 | 2.5 | 5 | i.t. | 50 | 4,5 | 17.7 ± 3.1 | 7.4 ± 0.3 |
| 18 | CPT in Vehicle 24 (suspension) | 5 | 10 | i.t. | 50 | 5,5 | 16.6 ± 1.6 | 6.8 ± 0.7 |

Group 4 3 animals were found dead on Days 10, 13, and 13; these numbers are used in the calculation
another animal had 29% weight loss by Day 8, however, recovered later with 4X at~19 days.
Group 13 1 animal had tumor site sloughing off by Day 3, then recored around Day 20.
Group 17 1 animal was found dead on Day 13, another one had no tumor.

EXAMPLE 17

Dose Response of Camptothecin in Suspension or in ADV24 on MBT-2 Tumor Growth

| | Treatment Group | Drug Conc. (mg/mL) | Drug Dose (mg/kg) | Inj. Site | Inj. Vol. (µL) | No. Tumors | 3X Tumor Growth (M ± SE in days) Treated | Untreated |
|---|---|---|---|---|---|---|---|---|
| 1 | untreated control | — | — | — | — | 9 | 5.7 ± 0.5 | |
| 2 | CPT suspension | 1.25 | 5 | i.p. | 100 | 9 | 5.9 ± 0.4 | |
| 3 | CPT suspension | 2.5 | 10 | i.p. | 100 | 8 | 7.2 ± 0.2 | |
| 4 | CPT suspension | 5 | 20 | i.p. | 100 | 10 | 6.2 ± 0.5 | |
| 5 | CPT suspension | 1 | 2 | i.t. | 50 | 5,5 | 6.4 ± 0.8 | 5.7 ± 0.3 |
| 6 | CPT suspension | 2.5 | 5 | i.t. | 50 | 5,5 | 8.6 ± 0.6 | 6.1 ± 0.5 |
| 7 | CPT suspension | 5 | 10 | i.t. | 50 | 5,5 | 9.6 ± 1.1 | 5.9 ± 0.7 |
| 8 | CPT suspension | 10 | 20 | i.t. | 50 | 4,5 | 13.8 ± 0.7 | 6.8 ± 0.4 |
| 9 | DMA/water (solvent control) | — | — | i.t. | 50 | 4,4 | 5.9 ± 0.2 | 5.5 ± 0.2 |
| 10 | Vehicle 24 (placebo control) | — | — | i.t. | 50 | 5,5 | 10.3 ± 0.8 | 5.4 ± 0.6 |
| 11 | CPT solution in DMA/water | 0.5 | 1 | i.t. | 50 | 5,5 | 15.8 ± 2.7 | 6.7 ± 1.1 |
| 12 | CPT solution in DMA/water | 1 | 2 | i.t. | 50 | 4,5 | 11.8 ± 1.4 | 6.0 ± 0.6 |
| 13 | CPT solution in DMA/water | 2.5 | 5 | i.t. | 50 | 5,5 | 12.5 ± 0.7 | 6.9 ± 0.5 |
| 14 | CPT solution in DMA | 5 | 10 | i.t. | 50 | 4,5 | 17.5 ± 5.0 | 6.3 ± 0.2 |
| 15 | CPT in Vehicle 24 | 0.5 | 1 | i.t. | 50 | 4,4 | 9.0 ± 1.4 | 6.1 ± 0.8 |
| 16 | CPT in Vehicle 24 | 1 | 2 | i.t. | 50 | 4,5 | 14.7 ± 1.4 | 5.1 ± 0.3 |

-continued

Dose Response of Camptothecin in Suspension or in ADV24 on MBT-2 Tumor Growth

| Treatment Group | Drug Conc. (mg/mL) | Drug Dose (mg/kg) | Inj. Site | Inj. Vol. (μL) | No. Tumors | 3X Tumor Growth (M ± SE in days) Treated | 3X Tumor Growth (M ± SE in days) Untreated |
|---|---|---|---|---|---|---|---|
| 17 CPT in Vehicle 24 | 2.5 | 5 | i.t. | 50 | 5,5 | 15.0 ± 3.4 | 5.9 ± 0.5 |
| 18 CPT in Vehicle 24 (suspension) | 5 | 10 | i.t. | 50 | 4,5 | 14.9 ± 3.3 | 7.8 ± 1.6 |

Group 14 1 cure
Deaths were attributed to metastasis and/or tumor burden on the untreated side

EXAMPLE 18

Antitumor Effect of Camptothecin (CPT) in Various Vehicles on Orthotopic N1-S1 Liver Tumors in Rats

| Treatment Group | Drug Conc. (mg/mL) | Drug Dose (mg/kg) | Inj. Site | Inj. Vol. (μL) | No. Tumors | Tumor Volume (mm³) day 0 | Tumor Volume (mm³) day 8 | Ratio (D-8/D-0) |
|---|---|---|---|---|---|---|---|---|
| 1 untreated control | — | — | — | — | 3 | 146 | 1214 | 8.3 |
|  |  |  |  |  |  | 59 | 452 | 7.7 |
|  |  |  |  |  |  | 132 | 838 | 6.3 |
|  |  |  |  |  | mean | 112 | 835 | 7.5/7.4 |
| 4 CPT suspension | 0.25 | 0.5 | i.p. | 400 | 4 | 250 | 2486 | 9.9 |
|  |  |  |  |  |  | 280 | 2155 | 7.7 |
|  |  |  |  |  |  | 114 | 1151 | 10.1 |
|  |  |  |  |  |  | 316 | 3532 | 11.2 |
|  |  |  |  |  | mean | 240 | 2331 | 9.7/9.7 |
| 5 CPT suspension | 2 | 0.5 | i.t. | 50 | 2 | 132 | 668 | 5.1 |
|  |  |  |  |  |  | 128 | 677 | 5.3 |
|  |  |  |  |  | mean | 130 | 673 | 5.2/5.2 |
| 6 CPT in DMA gel (Vehicle 24) | 2 | 0.5 | i.t. | 50 | 4 | 263 | 156 | 0.6 |
|  |  |  |  |  |  | 110 | 193 | 1.7 |
|  |  |  |  |  |  | 82 | 213 | 2.6 |
|  |  |  |  |  |  | 328 | 217 | 0.7 |
|  |  |  |  |  | mean | 196 | 195 | 1.0/1.4 |
| 7 CPT in DMA | 2 | 0.5 | i.t. | 50 | 2 | 128 | 90 | 0.7 |
|  |  |  |  |  |  | 235 | 195 | 0.8 |
|  |  |  |  |  | mean | 182 | 143 | 0.8/0.8 |

EXAMPLE 19

Dose Response of Camptothecin in ADV28 on MBT-2 Tumor Growth

| Treatment Group | Drug Conc. (mg/g gel) | Inj. Site | Inj. Vol. (μL) | No. Tumors | 4x Tumor Growth (M ± SE in days) |
|---|---|---|---|---|---|
| 1 untreated control | — | — | — | 8 | 7.8 ± 0.3 |
| 2 Vehicle 28 | — | i.t. | 25 | 8 | 8.7 ± 0.3 |
| 3 CPT in vehicle 28 | 1 | i.t. | 25 | 7 | 15.7 ± 1.2 |
| 4 CPT in vehicle 28 | 2 | i.t. | 25 | 7 | 14.1 ± 1.2 |
| 5 CPT in vehicle 28 | 5 | i.t. | 25 | 7 | 17.3 ± 2.1 |
| 6 CPT in vehicle 28 | 10 | i.t. | 25 | 8 | 16.4 ± 2.3 |

EXAMPLE 20

Antitumor Effect of Camptothecin in ADV29–31 on MBT-2 Tumor Growth

| Treatment Group | Drug Conc. (mg/g) | Inj. Site Inj. | Inj. Vol. (μL) | No. Tumors | 4x Tumor Growth (M ± SE in days) |
|---|---|---|---|---|---|
| 1 untreated control | — | — | — | 7 | 7.8 ± 0.3 |
| 2 Vehicle 29 (90/10 DMSO/H₂O) | — | i.t. | 50 | 7 | 11.9 ± 1.5 |
| 3 Vehicle 30 (40/50/10 DMSO/PEG300/H₂O) | | i.t. | 50 | 7 | 8.2 ± 0.6 |
| 4 Vehicle 31 (15/80/5 DMSO/PEG300/H₂O) | | i.t. | 50 | 7 | 8.7 ± 0.8 |
| 5 CPT in vehicle 29 | 1 | i.t. | 50 | 7 | 14.5 ± 1.6 |
| 6 CPT in vehicle 30 | 1 | i.t. | 50 | 7 | 13.2 ± 1.4 |
| 7 CPT in vehicle 31 | 1 | i.t. | 50 | 7 | 11.4 ± 0.9 |

The above results demonstrate that when an antiproliferative agent such as camptothecin is administered in a gelled (viscous) polar vehicle, the efficacy of the agent is significantly enhanced, as indicated by the increase in tumor growth delay, or the lower tumor volume at one week, as compared to that observed for the vehicle itself or the agent delivered in non-gelled polar vehicle. The above results also again demonstrate that the efficacy of an antiproliferative agent in a highly polar vehicle is enhanced as compared to that observed for the agent delivered in aqueous vehicles.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating a host suffering from a cellular proliferative disease, said method comprising:
    parenterally administering to said host at a target site at least proximal to a lesion associated with said cellular proliferative disease a composition comprising at least one antiproliferative agent in a pharmaceutically acceptable substantially non-aqueous delivery vehicle capable of acting as a depot for said agent, said vehicle comprising dimethyl sulfoxide in combination with at least one thickening agent, wherein said thickening agent is from about 0.5 to 10% (v/v) of said vehicle.

2. The method according to claim 1, wherein said composition is regionally administered.

3. The method according to claim 1, wherein said composition is intralesionally administered.

4. The method according to claim 1, wherein said cellular proliferative disease is a neoplastic disease.

5. The method according to claim 1, wherein said thickening agent is selected from the group consisting of fatty acids, fatty acid esters, aluminum or magnesium salts of fatty acids and crosslinked or noncrosslinked biocompatible polymers.

6. The method according to claim 1, wherein said antiproliferative agent is selected from the group consisting of cisplatin, camptothecin, vinblastine, paclitaxel, fluorouracil, doxorubicin, mechlorethamine, etoposide, mitomycin and bleomycin.

7. A method for treating a host suffering from a cellular proliferative disease, comprising intralesionally administering to said host a composition comprising an antiproliferative agent in a pharmaceutically acceptable substantially non-aqueous delivery vehicle capable of acting as a depot for said agent, said vehicle comprising dimethyl sulfoxide in combination with carboxypolymethylene and water, and further wherein said vehicle comprises less than about 15% (v/v) water.

8. The method according to claim 7, wherein said cellular proliferative disease is a neoplastic disease.

9. The method according to claim 7, wherein said antiproliferative agent is selected from the group consisting of cisplatin, camptothecin, vinblastine, paclitaxel, fluorouracil, doxorubicin, mechlorethamine, etoposide, mitomycin and bleomycin.

10. A method for treating a host with a cellular proliferative disease, comprising parenterally administering to said host a composition comprising an antiproliferative agent in a pharmaceutically acceptable substantially non-aqueous delivery vehicle capable of acting as a depot for said agent, said vehicle comprising dimethyl sulfoxide in combination with at least one thickening agent, wherein said thickening agent is from about 0.5 to 10% (v/v) of said vehicle, and further wherein said vehicle comprises less than about 15% (v/v) water.

11. The method according to claim 10, wherein said composition is regionally administered.

12. The method according to claim 10, wherein said composition is intralesionally administered.

13. The method according to claim 10, wherein said cellular proliferative disease is a neoplastic disease.

14. The method according to claim 10, wherein said thickening agent is selected from the group consisting of fatty acids, fatty acid esters, aluminum or magnesium salts of fatty acids and crosslinked or noncrosslinked biocompatible polymers.

15. The method according to claim 10, wherein said antiproliferative agent is selected from the group consisting of cisplatin, camptothecin, vinblastine, paclitaxel, fluorouracil, doxorubicin, mechlorethamine, etoposide, mitomycin and bleomycin.

* * * * *

UNITED STATES PATENT AND TRADEMARK OFFICE
CERTIFICATE OF CORRECTION

PATENT NO. : 6,669,958 B1  Page 1 of 1
DATED : December 30, 2003
INVENTOR(S) : George Trager et al.

It is certified that error appears in the above-identified patent and that said Letters Patent is hereby corrected as shown below:

Title page,
Item [56], References Cited, OTHER PUBLICATIONS, under "Theon et al.," change "Intratuloral" to -- Intratumoral --.

Column 3,
Line 5, change "f 50,000" to -- from about 500 to 50,000 --.

Column 17,
After last line in EXAMPLE 2 and before EXAMPLE 3, delete "20".

Column 19,
After last line in EXAMPLE 5 and before EXAMPLES 6 & 7, delete "25".

Columns 21 and 22,
After last line in EXAMPLE 8 and before EXAMPLES 9 & 10, delete "20".

Columns 31 and 32,
between EXAMPLE 19 and EXAMPLE 20, delete "45", "50", "55", "60", and "65".

Signed and Sealed this

Twenty-fifth Day of May, 2004

JON W. DUDAS
*Acting Director of the United States Patent and Trademark Office*